(12) United States Patent
Dickerson

(10) Patent No.: US 6,179,766 B1
(45) Date of Patent: Jan. 30, 2001

(54) METHODS OF BREAST CANCER TREATMENT

(76) Inventor: Gregg A. Dickerson, 4705 N. Lafern Way, Muncie, IN (US) 47304

( * ) Notice: Under 35 U.S.C. 154(b), the term of this patent shall be extended for 0 days.

(21) Appl. No.: 09/239,390

(22) Filed: Jan. 28, 1999

(51) Int. Cl.[7] ........................................................ A61N 5/00
(52) U.S. Cl. ...................................................................... 600/1
(58) Field of Search .................................. 600/1, 2, 3, 4; 604/19, 6.16

(56) References Cited

U.S. PATENT DOCUMENTS

| | | | |
|---|---|---|---|
| 4,190,461 | 2/1980 | Hedger | 134/1 |
| 4,427,005 | 1/1984 | Tener | 128/303 |
| 4,636,346 | 1/1987 | Gold et al. | 264/139 |
| 4,861,520 | 8/1989 | van'tHooft et al. | 252/644 |
| 5,084,001 * | 1/1992 | Van't Hooft et al. | 600/3 |
| 5,092,834 | 3/1992 | Bradshaw et al. | 600/7 |
| 5,120,323 * | 6/1992 | Shockey et al. | 604/282 |
| 5,199,939 | 4/1993 | Dake et al. | 600/3 |
| 5,282,781 | 2/1994 | Liprie | 600/3 |
| 5,395,300 | 3/1995 | Liprie | 600/3 |
| 5,452,720 | 9/1995 | Smith et al. | 128/653.1 |
| 5,498,227 | 3/1996 | Mawad | 600/3 |
| 5,503,614 | 4/1996 | Liprie | 600/7 |
| 5,531,662 | 7/1996 | Carr | 600/2 |
| 5,624,372 | 4/1997 | Liprie | 600/3 |
| 5,683,345 | 11/1997 | Waksman et al. | 600/3 |
| 5,695,457 * | 12/1997 | St. Goar et al. | 604/4 |
| 5,899,882 * | 5/1999 | Waksman et al. | 604/96 |
| 6,030,360 * | 2/2000 | Biggs | 604/95 |

OTHER PUBLICATIONS

Brasfield, M.D., Richard D. and Henschke, M.D., Ulrich K, "Intravascular Irradiation of the Internal Mammary Lymph Nodes in Breast Cancer." *Am. Journal of Roentgenology, Radium Therapy and Nuclear Medicine*, vol. 85, No.5 (1961) pp. 849–859.

Brasfield, M.D., Richard D.; Henschke, M.D., Ulrich and DasGupta, M.D., Taposh, "New Method of Treating Melanoma of the Pectoral Region." *American Journal of Surgery*, vol. 100 (1965) pp. 213–216.

Brasfield, M.D., Richard D. and Henschke, M.D., Ulrich, "New Technic for Treating Internal Mammary Node Metastases in Breast Cancer." *New York State Journal of Med.* vol. 22 (1961) pp. 3817–3819.

Brasfield, R.D. and Henschke, U.K., "Treatment of Internal Mammary Nodes with a Radioactive Wire." *International Union Against Cancer ACTA*, vol.20 (1964).

Brasfield, Richard D. and Henschke, Ulrich K., "Radioisotope Implantation into the Internal Mammary Vessels for Breast Cancer." *Surg. Forum*, vol. 10, (1959).

(List continued on next page.)

*Primary Examiner*—Max Hindenburg
*Assistant Examiner*—Brian Szmal
(74) *Attorney, Agent, or Firm*—Woodard, Emhardt, Naughton, Moriarty & McNett

(57) ABSTRACT

Methods for treating a tumor, a treatment catheter for treating a tumor and a kit for treating a tumor are described. In one aspect of the invention, a method for treating a tumor includes placing a radioactive material at a first predetermined site within an intact internal thoracic vessel for a time period sufficient to provide a therapeutically effective amount of radiation. Placing a radioactive material at a first predetermined site may include positioning a first catheter in the lumen of an intact internal thoracic vessel and placing a radiation source at a predetermined site within the lumen of the first catheter. The methods are advantageous for treating breast cancer, including breast cancer that has spread to the parasternal lymph nodes.

49 Claims, 9 Drawing Sheets

OTHER PUBLICATIONS

Henschke, Ulrich K; Hilaris, Basil S. and Mahan, G.D. "Afterloading in Interstitial and Intracavitary Radiation Therapy." *Am. Journal of Roentgenology, Radium Therapy and Nuclear Medicine*, vol. 90, No. 2 (1963) pp. 386–395.

Vermund, M.D., H and Kline, M.D., Joyce C. "Current Trends in Radiotherapy of Breast Cancer." *American Journal of Surgery*, vol. 106 (1963) pp. 430–439.

Urban, M.D., Jerome A. "Current Trends in Breast Cancer Treatment Part II." *New York State J. of Med.* (1961) pp. 3289–3301.

Margottini, Mario, "Mezzi Attuali Di Diagnosi E Di Terapia Del Carcinoma Della Mammella." Diagnosis and Therapy of Carcinoma of the Breast. Tumori, 53 (1967) pp. 65–79.

Brashfield, M.D., Richard D. and Henschke, M.D., Ulrich K, "Treatment of the Internal Mammary Lymph Nodes by Implantation of Radioisotopes into the Internal Mammary Artery." *Radiology* vol. 20 (1958) p. 259.

Andresov, N.S., Nechuskin, M.I. and Sushchikhine, M., "Treatment of parasternal nodes in patients with breast cancer." *Activity* (a Nucletron publication). Vol. 4, No. 2 (1990).

Cheng, M.D., Skye Hongiun et al., "The Benefit and Risk of Postmastectomy Radiation Therapy in Patients with High–Risk Breast Cancer." *Am. J. Clin. Oncol.* (CCT) vol.21, No. 1, pp. 12–17 (1998).

Syed, M.D., A.M. Nisar et al., "Combination of External and Interstitial Irradiation in the Primary Management of Breast Carcinoma." *Cancer*, vol. 46, pp. 1360–1365 (1980).

Overgaard, M.D., Marie et al., "Postoperative Radiotherapy in High–Risk Premenopausal Women with Breast Cancer who Receive Adjuvant Chemotherapy." *The New England Journal of Medicine*, vol. 337, No. 14, pp. 949–955 (1997).

Ragaz, Joseph et al., "Adjuvant Radiotherapy and Chemotherapy in Node–Positive Premenopausal Women with Breast Cancer." *The New England Journal of Medicine*, vol. 337, No. 14. pp. 956–962 (1997).

Evans, M.D., Gregory, "The Long–Term Effects of Internal Mammary Chain Irradiation and its Role in the Vascular Supply of the Pedicled Transverse Rectus Abdominis Musculocutaneous Flap Breast Reconstruction." *Annals of Plastic Surgery*, vol. 35. No. 4, pp. 342–348 (1995).

Elbeery, M.D., Joseph R. and Chitwood, Jr., M.D., Randolph, "Intraoperative Catheterization of the Left Internal Mammary Artery via the Left Radial Artery." *Ann. Thorac. Surg.*, vol. 64, pp. 1840–1842 (1997).

* cited by examiner

METHODS OF BREAST CANCER TREATMENT

FIELD OF THE INVENTION

The present invention relates generally to the field of adjuvant methods and devices for breast cancer treatment. Specifically, brachytherapy methods to treat a tumor, preferably a breast tumor, are described.

BACKGROUND OF THE INVENTION

One method of treating breast cancer is by radiotherapy. It may also be necessary to treat the parasternal lymph nodes as part of the course of breast cancer radiotherapy. Such radiotherapeutic treatment of the parasternal lymph nodes may lead to irradiation of large areas of normal tissue. This limits the total dose of radiation that can be delivered to the malignant tissue. Brachytherapy is a form of radiation therapy whereby a radiation source is placed in or near target malignant cells. One advantage of brachytherapy is the ability to deliver a higher dose of radiation while minimizing irradiation of normal tissue. Some methods of treating breast cancer, such as breast cancer metastases including metastases to the parasternal lymph nodes, include surgically cutting an internal thoracic artery and inserting a tube containing a source of radiation to treat parasternal lymph nodes after a mastectomy. This invasive procedure requires skilled surgeons, is mutilating and entails considerable risk for the patient, including post-operative infection. A minimally-invasive adjuvant method for treating breast cancer, such as breast cancer metastases, is needed. The present invention addresses this need.

SUMMARY OF THE INVENTION

Methods of treating a tumor are described. In one aspect of the invention, a method of treating a tumor includes placing a radioactive material at a first predetermined site within an intact internal thoracic vessel for a time period sufficient to provide a therapeutically effective amount of radiation. In this aspect of the invention, placing the radioactive material at a first predetermined site may include positioning a first catheter having a lumen extending longitudinally therethrough in the lumen of the intact internal thoracic vessel, preferably an artery, and positioning a radioactive material at a predetermined site within the lumen of the first catheter. The methods are advantageously used in the treatment of breast tumor metastases, especially metastases that effect the parasternal lymph nodes.

In a further aspect of the invention, a method of treating a tumor includes placing a first catheter having a lumen extending longitudinally therethrough into a femoral vessel, preferably an artery, advancing the first catheter into an internal thoracic vessel, preferably an artery, advancing a second catheter through the lumen of the first catheter wherein the second catheter has a lumen extending longitudinally therethrough, preferably having a closed distal end, and placing a radioactive material at a predetermined site within the lumen of the second catheter for a time period sufficient to provide a therapeutically effective amount of radiation. Other sites of entry to an internal thoracic vessel may include the radial vessel, brachial vessel or axillary vessel.

In yet another aspect of the invention, a treatment catheter is provided. The treatment catheter includes a first elongated tube having a proximal end, a distal end and a lumen extending longitudinally therethrough. The treatment catheter further includes a distal tip section including a proximal end, a distal end which is preferably closed and a lumen extending longitudinally therethrough. However, in yet other aspects of the invention, the distal tip section may be solid. The proximal end of the distal tip section abuts the distal end of the first elongated tube. The treatment catheter further includes a wire guide channel having a proximal end, a distal end and a lumen extending longitudinally therethrough. The wire guide channel extends along the longitude of the distal tip section. The lumen of the treatment catheter may advantageously house a radioactive material.

In yet another embodiment of the present invention, a kit for treating a tumor is provided. The kit includes an introducer, a first catheter having a proximal end, a distal end and a lumen extending longitudinally therethrough. The distal end of the first catheter advantageously has a curved configuration. The first catheter is also configured to introduce a second catheter inside a vascular passageway. The kit further includes a second catheter that includes a first elongated tube having a proximal end, a distal end and a lumen extending longitudinally therethrough. The second catheter further includes a distal tip section including a proximal end, a distal end which is preferably closed and a lumen extending longitudinally therethrough. In alternate embodiments, the distal tip section may be solid. The proximal end of the distal tip section abuts the distal end of the first elongated tube. The second catheter further includes a wire guide channel having a proximal end, a distal end and a lumen extending longitudinally therethrough. The wire guide channel extends along the longitude of the distal tip section. The lumen of the treatment catheter may advantageously house a radioactive material. In a preferred embodiment, the first catheter is an internal mammary artery guiding catheter.

It is an object of the invention to provide minimally-invasive and non-disfiguring methods of treating a tumor, such as breast tumors, and especially breast tumors that have spread to a lymph node, such as a parasternal lymph node.

It is a further object of the invention to provide methods of treating a tumor, such as breast tumors, and especially breast tumors that have spread to a lymph node, such as a parasternal lymph node, that minimize damage to normal tissue.

It is yet another object of the invention to provide a treatment catheter and a kit for treating a tumor, such as breast tumors, and especially breast tumors that have spread to a lymph node, such as a parasternal lymph node, that are advantageously used in a minimally-invasive method of treating a tumor.

These and other objects and advantages of the present invention will be apparent from the descriptions herein.

DESCRIPTION OF THE PREFERRED EMBODIMENT

For the purposes of promoting an understanding of the principles of the invention, reference will now be made to preferred embodiments and specific language will be used to describe the same. It will nevertheless be understood that no limitation of the scope of the invention is thereby intended, such alterations and further modifications of the invention, and such further applications of the principles of the invention as illustrated herein, being contemplated as would normally occur to one skilled in the art to which the invention relates.

As mentioned above, the present invention provides a treatment catheter, methods of treating a tumor and a kit for treating a tumor. In one aspect of the invention, adjuvant methods of treating breast cancer are provided. The methods include treating tumors arising through metastases of breast tumors, including breast tumors that have spread to, or are suspected of having spread to, a lymph node, including perivascular lymph nodes such as a parasternal lymph node. The methods take advantage of the fact that the parasternal lymph nodes lie along the length of and in close proximity to the internal thoracic vessels. Exposure of breast tumors that have spread to parasternal lymph nodes to a source of radiation disposed in a catheter in the lumen of an internal thoracic vessel, preferably an internal thoracic artery, according to the method disclosed allows delivery of a higher dose of radiation compared to irradiation of the parasternal lymph nodes with external irradiation through the chest wall while minimizing irradiation of normal tissues. Furthermore, the methods allow different sites within an internal thoracic vessel to be treated with different amounts of radiation. In one embodiment, a method of treating a tumor is described that includes placing a radioactive material at a first predetermined site within an internal thoracic vessel for a time period sufficient to provide a therapeutically effective amount of radiation. Placing the radioactive material at the predetermined site may include positioning a first catheter in the lumen of an intact internal thoracic vessel, preferably an artery, and placing the radiation source at a predetermined site within the lumen of the first catheter. In yet another aspect of the invention, a treatment catheter is described. The treatment catheter is advantageously configured to house a source of radiation for use in treating tumors, such as breast tumors, including breast tumors that have spread to lymph nodes, such as parasternal lymph nodes. In a further aspect of the invention, a kit for treating a tumor is provided that includes an introducer, a first catheter configured to introduce a second catheter into a vascular passageway and a second catheter configured to deliver a source of radiation.

Figure 1:
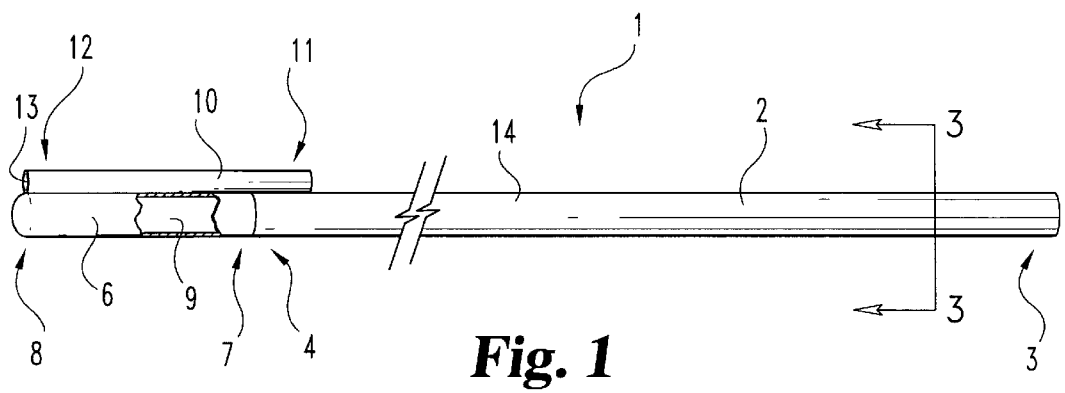
FIG. 1 depicts a side view of a treatment catheter.
Figure 2:
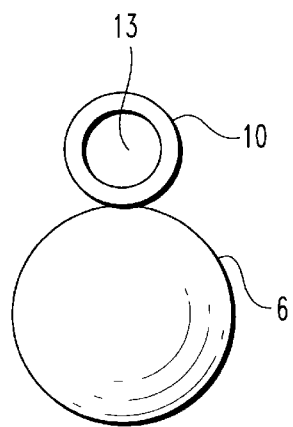
FIG. 2 depicts a distal end view of a treatment catheter.
Figure 3:
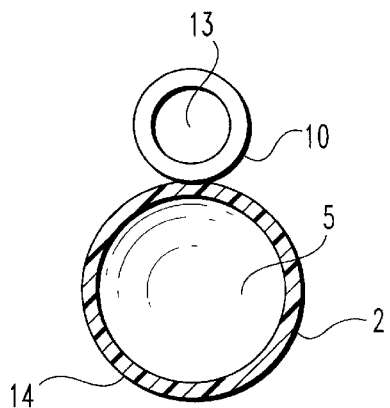
FIG. 3 depicts a proximal end view of a treatment catheter as viewed along line 3—3.

Referring to FIGS. 1–3, a treatment catheter 1 is shown that may be advantageously used in the adjuvant method of treating breast cancer. Treatment catheter 1 includes an elongated tube 2 having a proximal end 3, a distal end 4, a lumen 5 extending longitudinally therethrough and a distal tip section 6. The length of treatment catheter 1 may be chosen by one skilled in the art depending on the circumstances, but is preferably about 150 cm. Distal tip section 6 is also an elongated tube having a proximal end 7, a distal end 8, and a lumen 9 extending longitudinally therethrough. However, distal end 8 of distal tip section 6 is preferably closed in order to keep the radiation source that is ultimately disposed in lumen 2 and/or lumen 9 dry. The length of distal tip section 6 may be varied by one skilled in the art as needed, but is preferably about 4 cm. Proximal end 7 of distal tip section 6 abuts distal end 4 of elongated tube 2. More specifically stated, the central longitudinal axis of distal tip section 6 is preferably aligned with the central longitudinal axis of elongated tube 2. Proximal end 7 of distal tip section 6 may be secured to distal end 4 of elongated tube 2 by methods known in the art, including fusing. The inside diameter of elongated tube 2 and distal tip section 6 must be sufficiently large to allow passage of a commercial internal mammary artery guiding catheter therethrough while the outside diameter must be such that it will easily traverse through selected vascular passageways and may be chosen by one skilled in the art depending on the particular situation. However, the inside diameter of elongated tube 2 and distal tip section 6 is advantageously about 1.42 mm (4.2 French) and the outside diameter is advantageously about 1.67 mm (5 French) to about 2.0 mm (6 French). Moreover, lumen 5 of elongated tube 2 may advantageously house a radioactive material used in a method of treating a tumor. Furthermore, the radioactive material housed in lumen 5 may extend into lumen 9 of distal tip section 6.

Treatment catheter 1 also includes a second elongated tube, elongated tube 10, that extends along the longitude of elongated tube 2 and that is attached to outer surface 14 of elongated tube 2 by methods known in the art, including fusing. As seen in FIGS. 1–3, elongated tube 10 extends along the longitude of elongated tube 2. Elongated tube 10 has a proximal end 11, a distal end 12 and a lumen 13 extending longitudinally therethrough. Lumen 13 of elongated tube 10 is preferably configured to allow passage of a wire guide. Thus, elongated tube 10 may be used as a wire guide channel. The length of elongated tube 10 may be chosen by one skilled in the art depending on the circumstances. However, elongated tube 10 is preferably about 5 cm in length. The inside and outside diameters of elongated tube 10 may also be chosen by one skilled in the art depending on the circumstances. However, the inside diameter is preferably sufficiently large to accommodate a 0.36 mm (0.014 in) wire guide and the outside diameter must be small enough such that treatment catheter 1 can traverse selected vascular passageways. The inside and outside diameters of elongated tube 10 are advantageously about 0.67 mm (2 French) and 1 mm (3 French), respectively. In yet an alternate embodiment, elongated tube 10 may extend along the entire length of elongated tube 2. In such an embodiment, both elongated tubes 2 and 10 may be co-extruded by methods known to the art.

Figure 4:
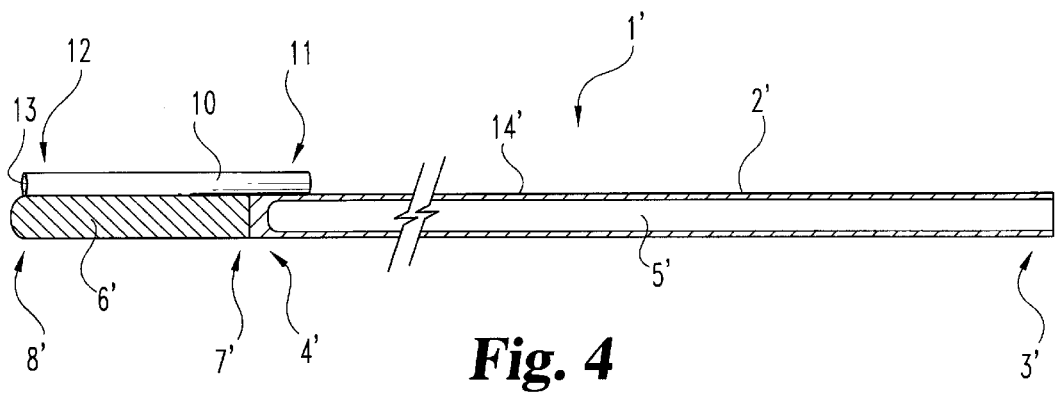
FIG. 4 depicts a side view of an alternate embodiment of a treatment catheter.

In yet another embodiment as shown in FIG. 4, distal tip section 6' may be solid, which allows for increased flexibility of treatment catheter 1'. In this embodiment, it is preferred that elongated tube 2' be closed at distal end 4' for ease of joining elongated tube 2' to distal end 7' of distal tip section 6'. Distal end 8' of distal tip section 6' is also shown, as is elongated tube 10, and outer surface 14' and lumen 5' of elongated tube 2'.

Elongated tubes 2, 2' and 10 and distal tip section 6 and 6' are preferably constructed from any material as known in the art that will give the catheter flexibility so that it can make up to about 90° turns but will be sturdy enough so that it will not be fractured or perforated by, for example, a wire guide (or source cable as discussed below) during the procedure. Such materials include, for example, polytetrafluoroethylene (Teflon), polyethylene, polyurethane, nylon or a combination thereof. In one especially preferred form, elongated tubes 2 (and 2') and 10 are constructed from nylon. Distal tip section 6 (and 6') is preferably comprised of a material of lower durometer (i.e., a softer material allowing for more flexibility) than either elongated tube 2 (or 2') or 10, thus providing increased flexibility to traverse vascular passageways.

Elongated tube 2 (and 2') and distal tip section 6 (and 6') may be comprised of a single layer of material or may be comprised of multiple layers, such as two or three layers. Furthermore, one or more layers of braiding may also be included in constructing treatment catheter 1. For example, elongated tube 2 may include an inner layer of nylon as described above surrounded by a layer of braiding, such as braided stainless steel fiber laid down in a conventional manner by a braiding machine as known in the art. The stainless steel layer is further preferably surrounded by another layer of nylon by methods known in the art. Moreover, distal tip section 6 (and 6') may further be constructed to have a radiopaque agent as known in the art to assist in fluouroscopic localization of the catheter.

In another more preferred embodiment, the treatment catheter may be a Nucletron Lumencath catheter, from Nucletron Corporation, Columbia, Md., as known in the art and as described in Nucletron's 1998 product catalog at catalog number 089.078. Moreover, the Nucletron catheter may be steered by devices known to the art, including guide wires. The Nucletron catheter is preferably steered with a steerable guide wire including a deflection push/pull handle as known in the art having two finger rings, a thumb ring and wherein the deflection handle is connected to a guide wire. The guide wire attached to the deflection handle is inserted into the lumen of the treatment catheter, preferably the lumen of the Lumencath catheter, and the thumb ring is depressed in order to vary the curvature of the catheter as desired. Such a catheter deflection set is preferably obtained from Nucletron as more fully described in Nucletron's 1998 product catalog at catalog number 090.681. However, the length of the guide wire is preferably about 150 cm.

In yet another aspect of the invention, a method of treating a tumor is provided which includes positioning a catheter in the lumen of an intact internal thoracic vessel, preferably an artery, and placing a radiation source at a predetermined site within the lumen of the catheter, advantageously in an area that is contained within the internal thoracic vessel. The radiation source remains in the lumen of the catheter for a time period sufficient to provide a therapeutically effective amount of radiation. FIGS. 4–11 depict various steps in the method of the present invention and show the locations of various anatomical structures. A brief discussion of the location of the anatomical structures follows prior to a detailed discussion of various aspects of the methods of the present invention.

Figure 5:
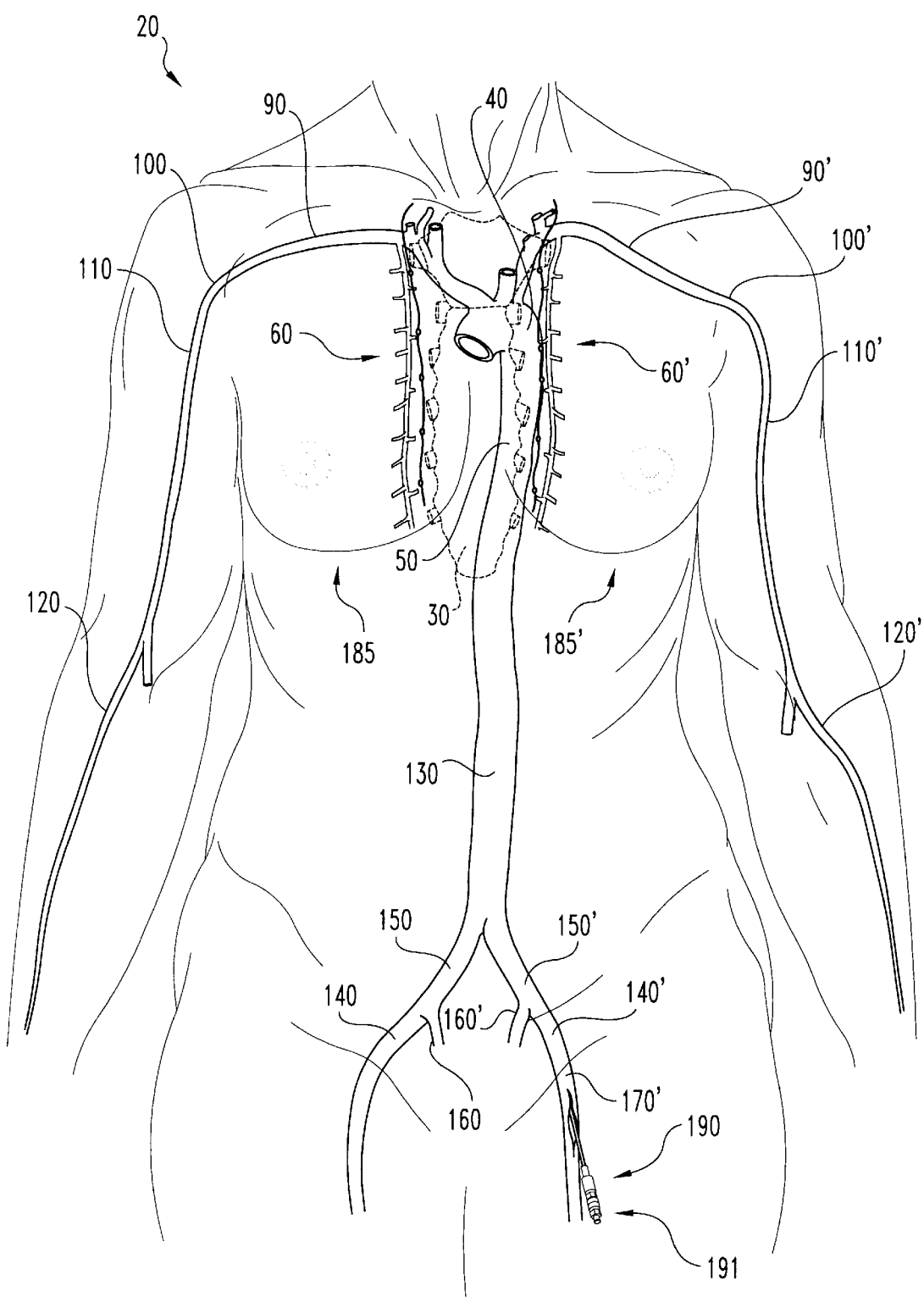
FIG. 5 is a view of the upper body of a human female depicting a schematic representation of a step in one embodiment of a method of treating a tumor.
Figure 6:
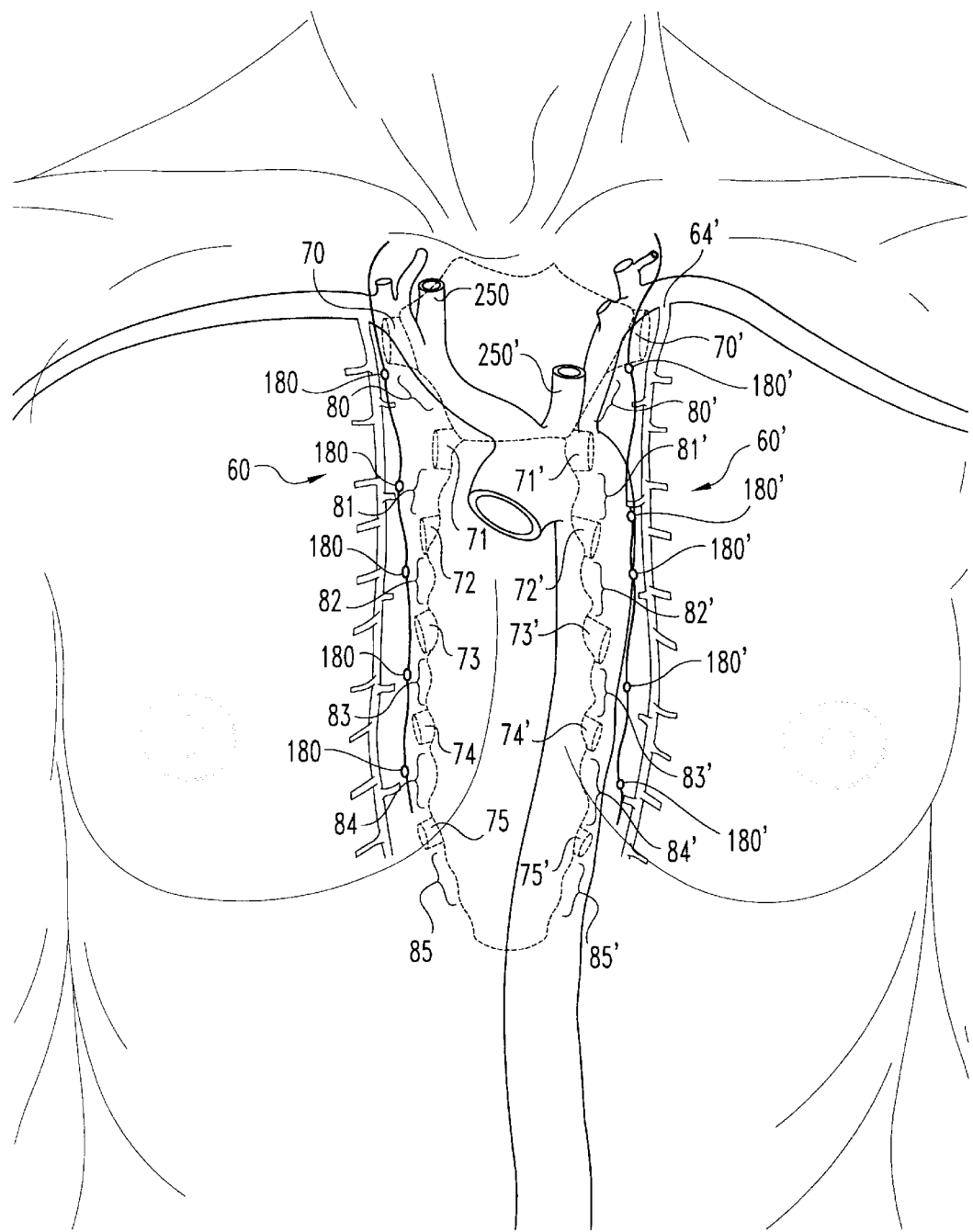
FIG. 6 is an enlarged view of the upper body of the human female of FIG. 5.

Referring to FIGS. 5 and 6, vascular passageways and other anatomical structures of a human female 20 are shown. FIGS. 5 and 6 only show selected anatomical structures so as to serve as a guide for the methods of the present invention. More anatomical structural information may be found in standard anatomy textbooks as known in the art. As most of the structures discussed are present on the left and right sides of the body, structures designated with a particular number with a prime represent the same structures on the left side of the body as the structures on the right side of the body designated by the same numeral without the prime. The sternum 30 overlies the aortic arch 40 and thoracic aorta 50 but is drawn with dotted lines as it is present to show the environment. The internal thoracic arteries 60 and 60' are shown that independently descend behind upper six ribs 70–75 and 70'–75', respectively. Upper six intercostal spaces 80'–85' lie between respective ribs 70'–75'. Also seen in FIG. 5 is subclavian artery 90', from which internal thoracic artery 60 branches, axillary artery 100', brachial artery 110', radial artery 120', abdominal aorta 130, external iliac artery 140', common iliac artery 150', internal iliac artery 160' and femoral artery 170'. Five parasternal lymph nodes 180 are also shown, as best seen in FIG. 6, although this number may vary in certain individuals due to anatomical variation as known in the art. Parasternal lymph nodes 180 and 180' actually lie along internal thoracic artery 60 and 60', respectively, but are shown in FIGS. 5 and 6 to the side of the respective internal thoracic arteries so that the internal thoracic arteries can be clearly seen. Breasts 185 and 185' are also shown.

Figure 7:
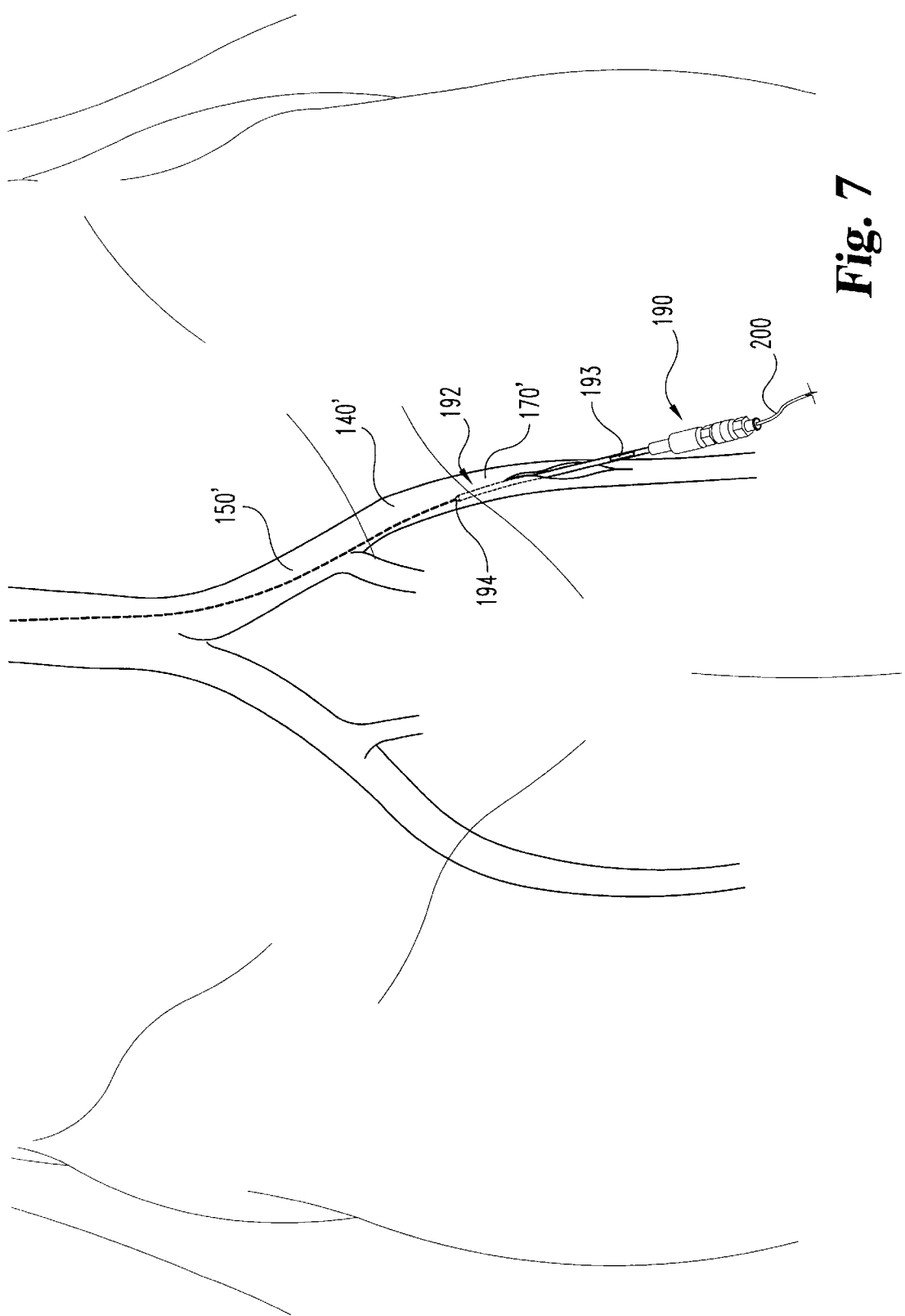
FIG. 7 is an enlarged view of the lower body of the human female of FIG. 5, showing a step in one embodiment of a method of treating a tumor.
Figure 8:
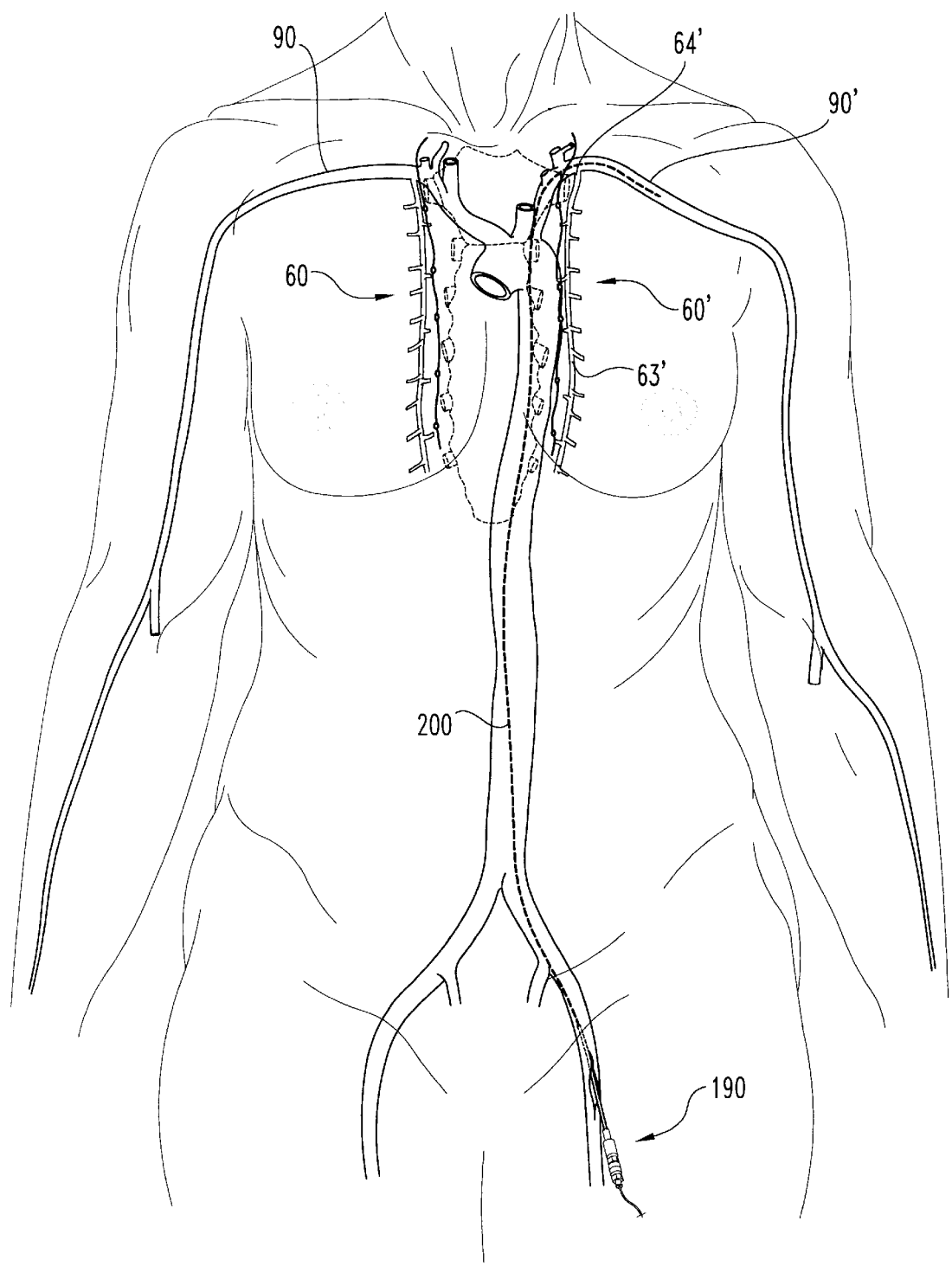
FIG. 8 is a schematic representation of another step of the method of treating a tumor depicted in FIG. 7, showing a wire guide being placed through the femoral artery and into a subclavian artery.

In one embodiment of a method of treating a tumor as depicted in FIGS. 5 and 7–8, a femoral vessel is used as an entry point into the lumen of an internal thoracic vessel. In a preferred embodiment, after the patient is prepped in a sterile manner and the patient's leg is draped as known in the art, an introducer 190 is used to enter a femoral artery. Either femoral artery can be selected. Introducer 190 is any standard introducer as known in the art having a proximal end 191, a distal end 192 and a lumen 193 of inside diameter that is greater than an outside diameter of a commercially available internal mammary artery guiding catheter and a needle 194 at the distal end. Although the inside and outside diameters of introducer 190 may vary, the outside diameter of the introducer is typically about 2.3 mm (7 French) to about 2.7 mm (8 French) whereas the internal diameter is preferably about 2.6 mm (8 French) After introducer 190 has pierced femoral artery 170', wire guide 200, preferably about a 0.89 mm (0.035 in) diameter wire guide and constructed from materials as known in the art, including metals such as stainless steel, is advanced from proximal end 191 of the introducer, through lumen 193 of the introducer, and out distal end 192 of the introducer into femoral artery 170' as seen in FIGS. 7 and 8. Wire guide 200 is further advanced, under fluoroscopic guidance as known in the art, through external iliac artery 140', common iliac artery 150', abdominal aorta 130, thoracic aorta 50 and is finally positioned so that it points into either right subclavian artery 90 or left subclavian artery 90', depending on whether right internal thoracic artery 60 or left internal thoracic artery 60' is to be treated. FIG. 8 shows wire guide 200 positioned in the left subclavian artery 90', preferably past opening 64' to lumen 63' of internal thoracic artery 60'.

Figure 9:
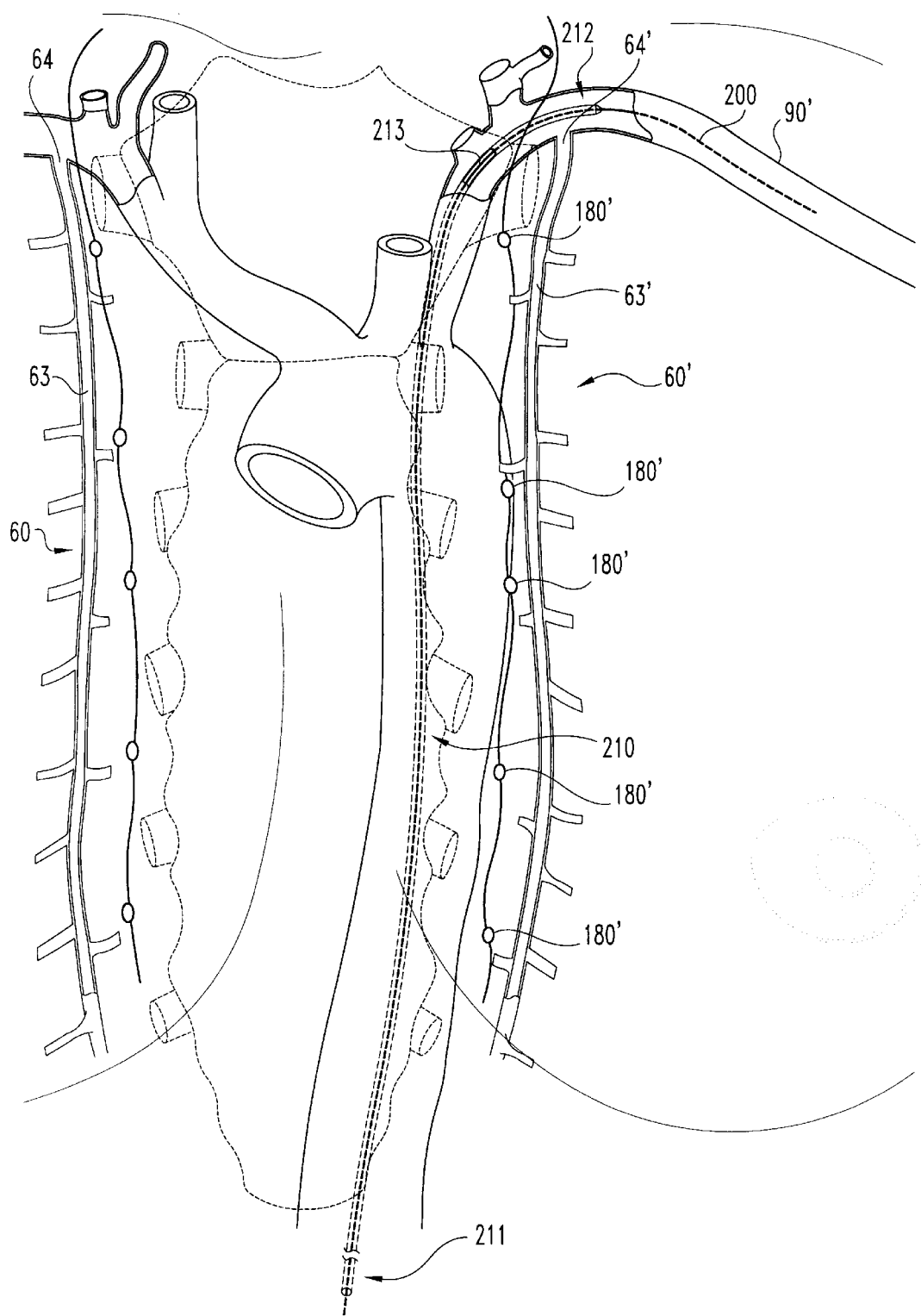
FIG. 9 is a schematic representation of a further step of the method of treating a tumor depicted in FIG. 8, showing positioning of an internal mammary artery guiding catheter in the subclavian artery.
Figure 10:
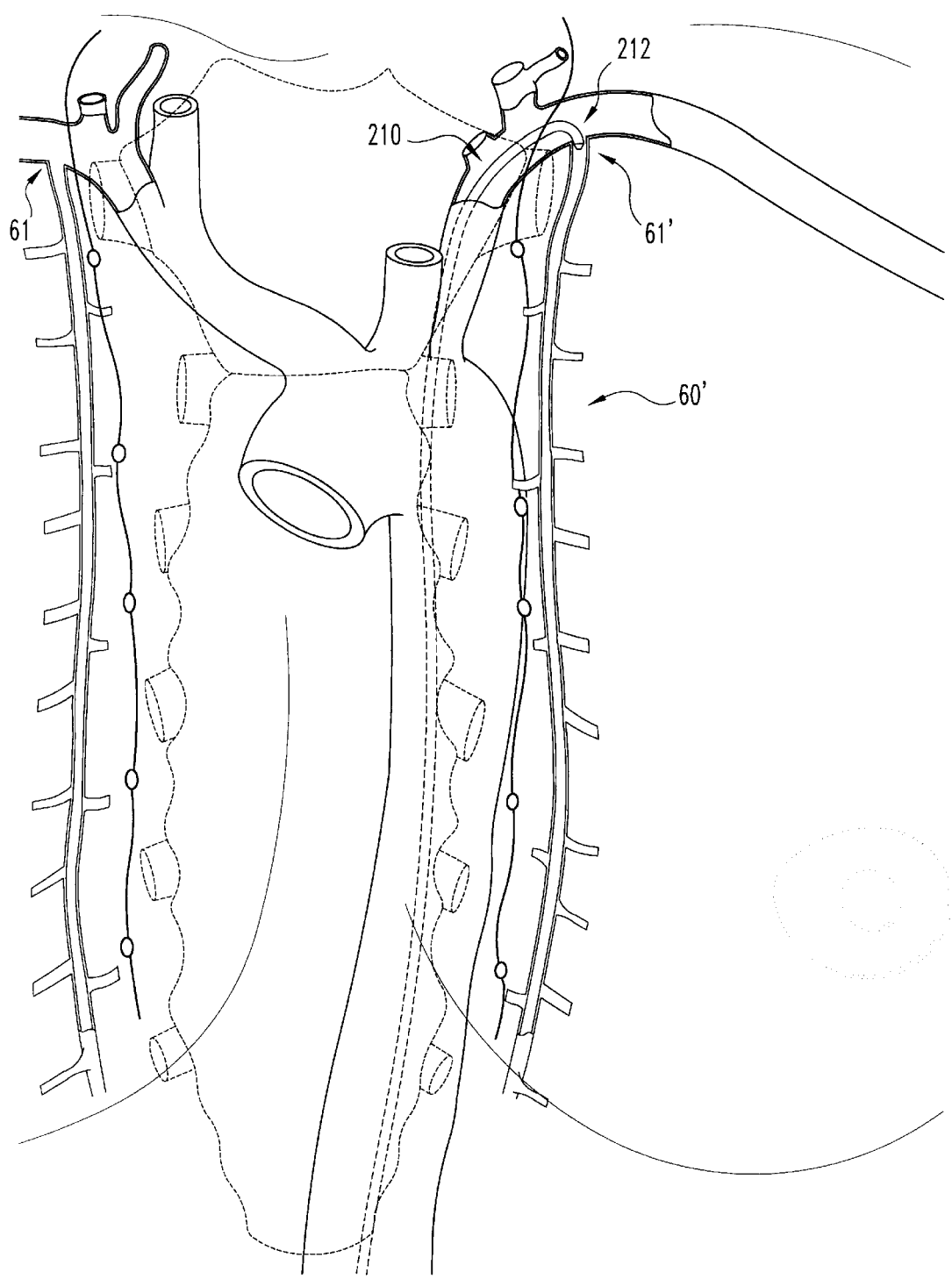
FIG. 10 is a schematic representation of yet another step of the method of treating a tumor depicted in FIG. 9, showing positioning of an internal mammary artery guiding catheter in a proximal region of an internal thoracic artery.

Referring next to FIG. 9, in order to treat left internal thoracic artery 60', an internal mammary artery guiding catheter 210 as known in the art is advanced along wire guide 200 and is positioned in left subclavian artery 90'. Internal mammary artery guiding catheter 210 is an elongate tube having a proximal end 211, a distal end 212 and a lumen 213 extending longitudinally therethrough. Distal end 212 of internal mammary artery guiding catheter 210 preferably has a curved configuration which becomes straightened when mounted on wire guide 200 in order to traverse the vascular passageways. Although the inside and outside diameters of internal mammary artery guiding catheter 210 may be chosen as needed by one skilled in the art, keeping in mind that the diameters should be chosen such that a treatment catheter will be able to pass through it easily, internal mammary artery guiding catheter 210 preferably has an outside diameter of about 7 French (2.3 mm) or 8 French (2.7 mm) and an inside diameter of about 2.2 mm. Moreover, guiding catheter 210 should also preferably allow continuous blood flow or at least occlude blood flow only temporarily during treatment. Any such guiding catheter for use in branching blood vessels may be used, such as the catheter described in U.S. Pat. No. 4,636,346 to Gold et al. which is hereby incorporated by reference in its entirety. FIG. 9 depicts internal mammary artery guiding catheter 210 positioned in left subclavian artery 90', just past opening 64' to lumen 63' of internal thoracic artery 60'. After internal mammary artery guiding catheter 210 is appropriately positioned, wire guide 200 may be completely removed from lumen 213 of guiding catheter 210 and x-ray dye may be introduced through the lumen of internal mammary artery guiding catheter 210 in order to fluoroscopically visualize internal thoracic artery 60' by procedures well known in the art. Other procedures known in the art may also be used to localize the internal thoracic vessel, including digital subtraction angiography. Internal mammary artery guiding catheter 210, with its distal end 212 in a hooked or curved configuration after removal of wire guide 200, is manipulated or torqued in order to selectively engage internal thoracic artery 60' and thereby position proximal end 211 of internal mammary guiding catheter 210 into proximal portion 61' of internal mammary artery 60' as seen in FIG. 10.

A wire guide 220 is then advanced into femoral artery 170', through external iliac artery 140', common iliac artery 150', abdominal aorta 130, thoracic aorta 50, subclavian artery 90' and into and through lumen 63' of internal thoracic artery 60' as far distally as possible, advantageously past about $5^{th}$ intercostal space 84' Wire guide 220 is preferably about 0.36 mm (0.014 in) in diameter. A treatment catheter 1 is then threaded on wire guide 220 over elongated tube 10 and advanced into lumen 213 of guiding catheter 210.

The treatment catheter used is not critical as long as it has sufficient flexibility to make 90° turns but is sturdy enough so that it will not be fractured or perforated during the procedure. The treatment catheter should also preferably have a closed distal end so that the radiation source ultimately disposed in the lumen of the treatment catheter is kept dry. Moreover, it is preferable that the treatment catheter have a wire guide channel. In one preferred embodiment, treatment catheter 1 described herein may be used.

Figure 11:
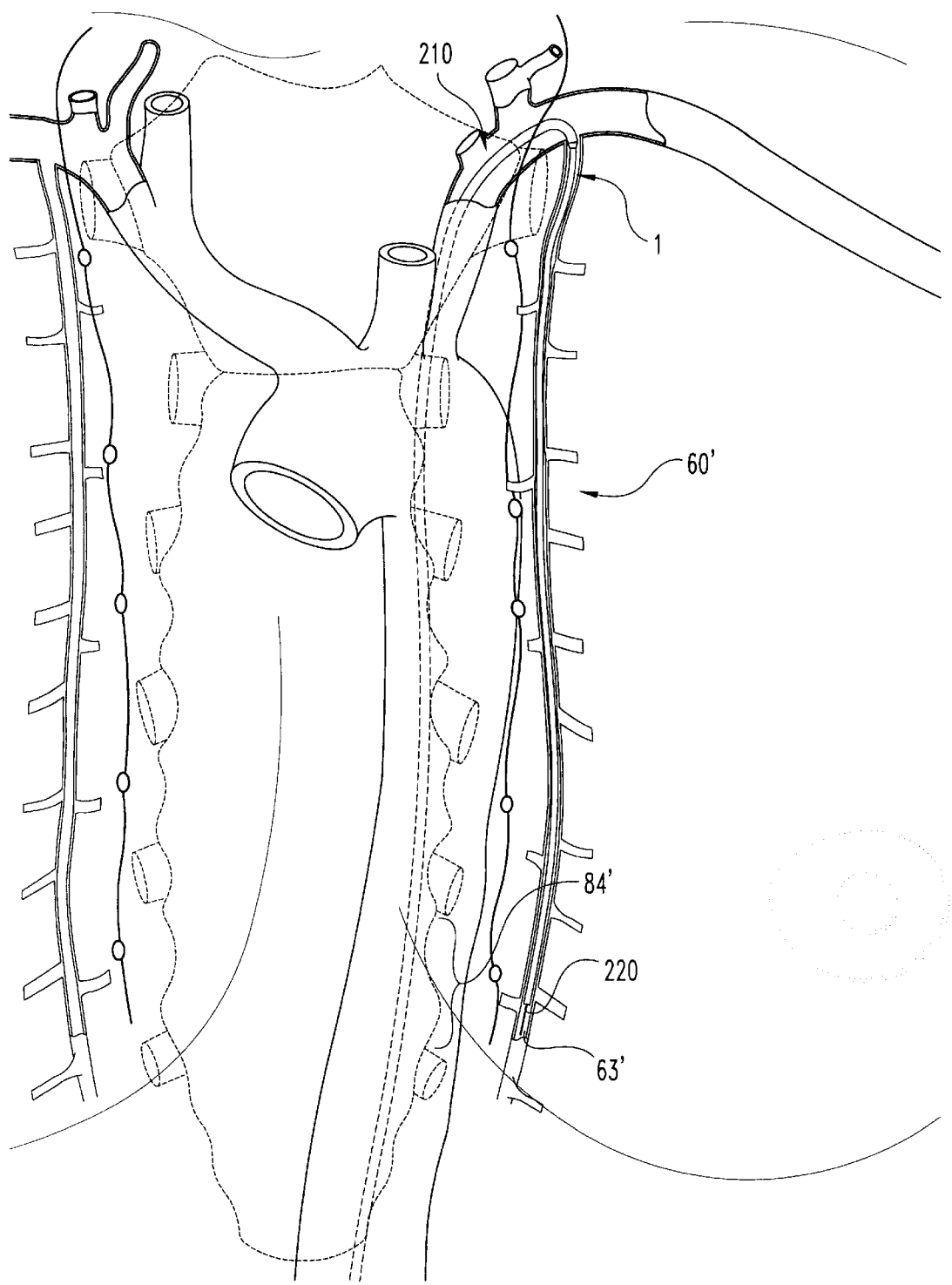
FIG. 11 is a schematic representation of a further step of the method treating a tumor depicted in FIG. 10, showing positioning of a treatment catheter in the lumen of an internal thoracic artery.

In the preferred embodiment using treatment catheter 1, after threading elongated tube 10 of treatment catheter 1 on wire guide 220 and advancing the catheter into lumen 213 of guiding catheter 210, treatment catheter 1 may advantageously be further advanced into lumen 63' of internal thoracic artery 60'. Treatment catheter 1 is shown positioned at the level of the $5^{th}$ intercostal space 84' as depicted in FIG. 11. Radiographs are taken for verification of catheter placement and treatment planning. Contrast may be injected through internal mammary artery guiding catheter 210 as long as the treatment catheter is not occluding the artery so that blood flow may be documented which may assist in treatment planning. The patient may also require therapeutic heparinization to prevent thrombosis. The heparin may be delivered intravenously as known in the art. Once treatment catheter 1 is appropriately positioned, the access port in the leg is secured and the patient is draped so the insertion field remains sterile. The patient is then transferred to the radiation therapy unit for further treatment planning radiographs and/or subsequent radiation treatment.

In a further embodiment of the invention, a method of treating a tumor, preferably a breast tumor and further preferably a breast tumor that has spread to a lymph node, preferably a parasternal lymph node, is provided including positioning a first catheter in a vessel that is continuous with a vessel that branches into an internal thoracic vessel, advancing the first catheter into the internal thoracic vessel and placing a radiation source at a predetermined site within the lumen of the catheter for a time period sufficient to provide a therapeutically effective amount of radiation. Vessels continuous with an internal thoracic vessel include the radial vessels, brachial vessels and axillary vessels. A similar procedure is carried out as for entry into an internal thoracic vessel through a femoral vessel. For example, sterile preparation and draping of the arm as known in the art is performed. In a preferred embodiment, the positioning of the first catheter includes placing a second catheter into the appropriate radial artery, brachial artery or axillary artery, advancing the second catheter into the internal thoracic artery, preferably through the lumen of an axillary artery and a subclavian artery in the case of entry through the brachial artery or through the brachial and axillary artery if entry is through a radial artery, and advancing the first catheter, distal end first, through the lumen of the second catheter. The first catheter is then further preferably advanced into the lumen of the appropriate internal thoracic artery to about the level of the $5^{th}$ intercostal space as described above. In a preferred embodiment, the first catheter is a treatment catheter 1 and the second catheter is an internal mammary artery guiding catheter 210. Other internal thoracic artery access points as known in the art may also be used, even though they are non-preferred access points, including the carotid artery 250 or 250', as seen in FIG. 6.

In an embodiment utilizing the venous system in a method of treating a tumor, an identical procedure may be carried out as above. The veins lie along their respective arteries as known in the art. In one embodiment, the internal thoracic vein, which lies alongside the internal thoracic artery, may be accessed by entry through the femoral vein. In this embodiment, the path to the internal thoracic vein is from the femoral vein, through the external iliac vein, the common iliac vein, the vena cava and the subclavian vein. When accessing an internal thoracic vein through the radial vein, the path to the internal thoracic vein is through a radial vein, an axillary vein and a subclavian vein. Besides the pathway for treatment, the only other difference between accessing an internal thoracic vessel through the venous system compared to the arterial system is in the method of identifying the internal thoracic vein. If dye is used to visualize an internal thoracic vein as used in the arterial system, it will be necessary to inject the dye in a vein known in the art that is distal from the respective internal thoracic vein due to the fact that blood is flowing to the heart in a distal to proximal direction. However, other methods of identifying an internal thoracic vein may be used as known in the art, including digital subtraction angiography.

Although the methods are preferably applied to breast tumors that have spread to lymph nodes, such as parasternal lymph nodes, the methods are also advantageous in treating tumors that are close enough to the internal thoracic vessels to receive a therapeutic dosage of radiation. For example, melanomas and sarcomas on the chest wall may be treated with the methods of the present invention.

Radiation can be delivered to parasternal lymph nodes 180' by any method known in the art but it is preferably delivered by a method involving High Dose Rate (HDR) brachytherapy. In this method, a radioactive material 230 is delivered to predetermined sites within a treatment catheter lumen positioned within an internal thoracic vessel for predetermined periods of time and then removed. The radiation is preferably delivered by a remote afterloading machine as known in the art, including a VariSource high dose rate remote afterloader but preferably a Nucletron microSelectron high dose rate remote afterloader. As the high dose rate remote afterloaders are well known in the art and the Varisource remote afterloader is described in detail in U.S. Pat. No. 5,092,834 to Bradshaw et al. and is hereby incorporated by reference in its entirety, no detailed discussion of the afterloaders is provided herein. However, the remote afterloaders typically include a mobile base, a safe to shield the radioactive source, a drive mechanism, an emergency motor, an indexer for moving the source to selected catheters, an emergency mechanical retraction system, a source position monitoring system, backup batteries and a simulated (dummy) source and cable.

The radioactive source used with the remote afterloading unit may be any source known in the art, including cobalt-60, cesium-137, iridium-192, iodine-125, palladium-103, tantalum-73, tungsten-74 and gold-198. However, iridium-192 is the preferred source. The radiation source may be contained as known in the art. For example, in the Nucletron microSelectron HDR remote afterloader, the source is typically contained in a source capsule 5 mm long with a 1.1 mm outside diameter. The capsule is welded to a stainless steel drive cable of the same outer diameter. The cable, in turn, is housed in the safe of the remote afterloader.

The strength of the source of radiation is typically about 3 Ci to about 10 Ci, but is preferably about 10 Ci. The determination of total dose, fraction size and interfraction interval (i.e., the span of time between administration of respective fractions) ultimately is a clinical decision that is made after careful review of all clinical, pathological and radiologic data and should be critically evaluated on an individual basis for each patient. Moreover, dosages that will achieve a therapeutically effective amount of radiation will depend on factors including the extent of the metastasis, whether chemotherapy is administered and the general health of the patient as known in the art. However, a total dose of about 4000 cGy to about 5000 cGy is typically given at each location treated, but preferably about 4000 cGy is given, when chemotherapy is not administered. When chemotherapy is administered, a total dose of about 4500 cGy to about 5000 cGy, preferably about 4500 cGy, is administered. The dose is typically administered in a multifraction regimen as known in the art. For a dose of about 4500 cGy, a fractionated dose of 2700 cGy that will be equivalent to 4500 cGy must be delivered as calculated by the Ortin conversion as known in the art and as discussed in Warmelink et al., *Proceedings of the 5$^{th}$ International Selectron User's Meeting* 1988 The Hague-The Netherlands, pp. 41–48 (1988) which is hereby incorporated by reference in its entirety. The dose is preferably given in 4 fractions of 675 cGY. Two fractions are preferably given at one time with at least a 6 hour interfraction interval and the following two fractions are given about 7 to about 10 days later. Four fractions of 675 cGy is further found to be approximately equivalent to 4500 cGy by the California Endocurietherapy Cancer Center's "HDR to Extrapolated Response Dose Conversion Table" published in *High Dose Rate Brachytherapy Treatment Protocols, California Endocurietherapy Cancer Center*, Oakland, Calif. (1996) which is hereby incorporated by reference in its entirety.

The length of the selected internal thoracic vessel, preferably an artery, from its proximal end up to about the 3$^{rd}$ intercostal space is preferably treated. However, depending on the circumstances, the length of the internal thoracic vessel from its proximal end up to the 4$^{th}$ or 5$^{th}$ intercostal spaces 83' and 84', respectively, or up to further distal sites, may be treated. This length of the internal thoracic vessel may be divided into smaller lengths that will be treated individually for a specified dwell time established during the treatment planning period.

The treatment planning procedure involves two steps as known in the art: 1) obtaining the source and treatment catheter geometry while the source and treatment catheter are positioned in the patient and 2) calculation of dwell times (i.e., the time the source remains at a particular site) for the HDR radiation source. The first step is advantageously accomplished by orthogonal film radiography or computerized axial tomography as known in the art. Dummy markers are used in the treatment catheter in lieu of the radioactive material 230 to allow visualization. A computerized axial tomography scan of the sternum and internal thoracic vessels further yields information as to the location of internal thoracic vessels which may be used advantageously in the planning of additional radiation therapy to be administered to adjacent sites in the course of breast cancer treatment. Computerized axial tomography may also yield information regarding the proximity of critical structures, such as the heart, so that the dose administered may be selectively reduced to the critical structure and remain therapeutically adequate to the parasternal lymph nodes. Moreover, computerized axial tomography also yields information as to the location of enlarged parasternal lymph nodes so these sites may specifically be treated with a therapeutic dose. The images may be input into treatment planning computer systems as known in the art through a digitizer or ethernet link. The second step is accomplished by taking into account the distance of the target tumor from the radiation source, the incremental length of the internal thoracic vessel that is being treated and the absolute dose to be delivered. Dwell time calculation and optimization may be accomplished by commercial treatment planning packages as known in the art, including Nucletron Plato®. The dwell time calculations are based on well-established physical characteristics of the source utilized, such as the Iridium-192 HDR source.

Figure 12:
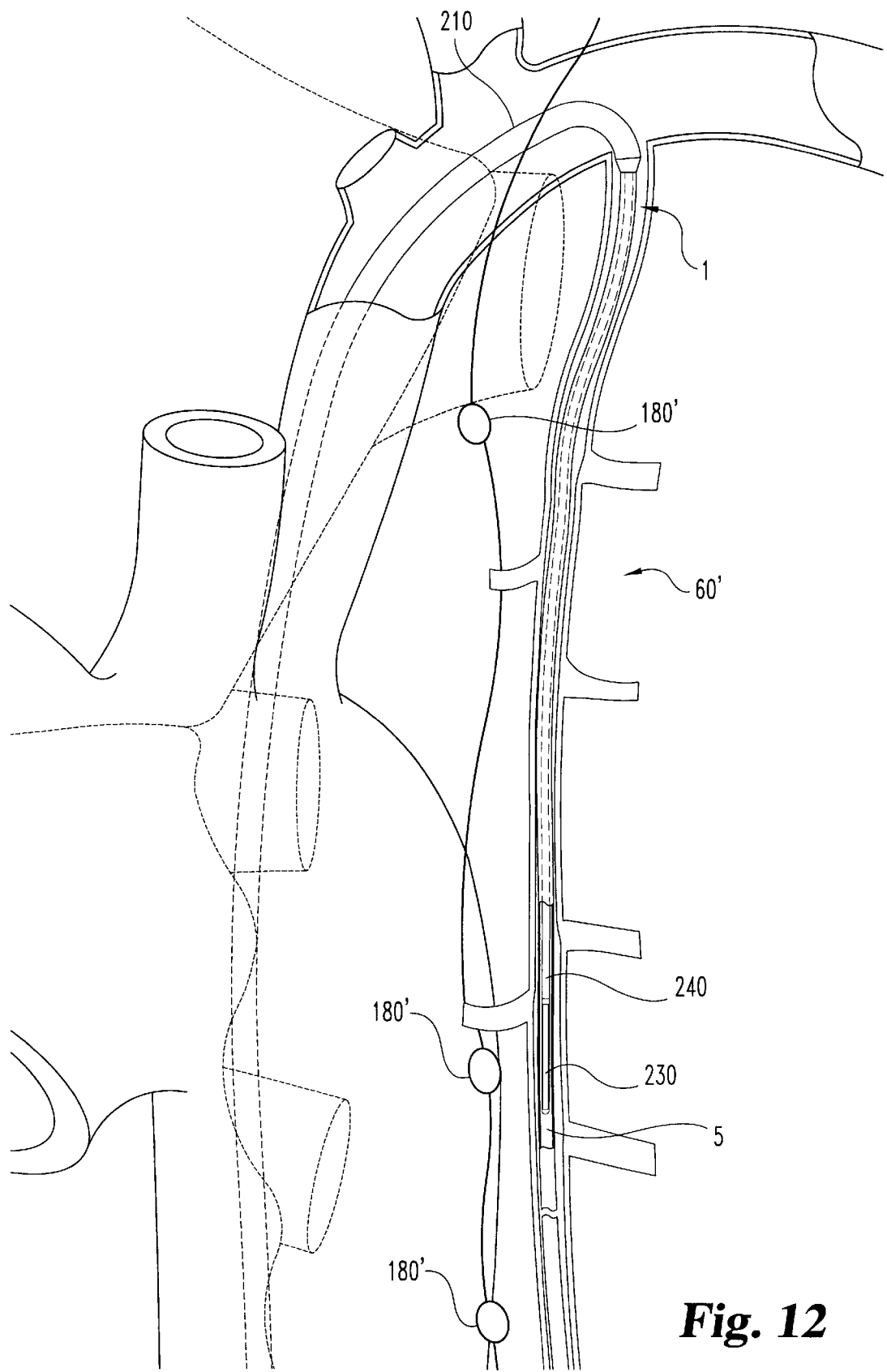
FIG. 12 is a schematic representation of a further step of the method of treating a tumor depicted in FIG. 11, showing treatment of parasternal lymph nodes with a radiation source disposed in the lumen of a treatment catheter.

The first fraction of radiation is delivered after treatment catheter 1 is positioned as described above. Positioning of treatment catheter 1 is preferably reverified by fluoroscopic methods prior to administering the first fraction of radiation. The test cable of the remote afterloader is passed and retracted to verify satisfactory source transfer capability prior to administering the treatment. FIG. 12 shows radioactive material 230 contained within source cable 240 which is disposed in lumen 5 of treatment catheter 1. The time that the radioactive material 230 remains in place at the predetermined site in the internal thoracic vessel will vary as discussed above with respect to treatment planning. For example, utilizing a 6.5 Ci source as radioactive material 230 to deliver four fractions each of 675 cGy, and assuming the tumor target is within about 5 mm of the external surface of the internal thoracic vessel (about 7 mm to about 8 mm from the radiation source) and the incremental length of the internal thoracic vessel is about 150 mm, the source must stay in place for a period of about 4 minutes for each fraction of radiation delivered. Radioactive material 230 is then moved distally to the next predetermined site until all sites along the selected length of the internal thoracic vessel are treated with the first treatment. After the treatment has been administered, radioactive material 230 is withdrawn and the following treatment fraction is administered with at least a 6 hour interfraction interval between treatments. In a preferred embodiment, the patient is observed typically about 8 hours to about 16 hours prior to being discharged. The next two treatment fractions are administered in a similar fashion about 7 to about 10 days later. Alternatively, the next two treatment fractions may be administered at 6 hour interfraction intervals prior to discharging the patient. In such a case, the treatment catheter may be removed after about 18 hours and heparinization is then discontinued. The former treatment regimen is preferred due to the risks of arterial catheterization and heparinization for a continuous period of about 18 hours or more. The transit dose for a microSelectron HDR unit is known to be 0.31 cGy/Ci/fraction at 5 mm from the catheter as reported by Bastian, Podgorsak and Thomadsen, *International Journal of Radiation Oncology, Biology and Physics* 26:695–702 (1993). This would result in a transit dose for a 6.5 Ci source of 2 cGy/fraction at 5 mm from the catheter.

In yet another embodiment, chemotherapeutic agents may be administered to the patient either before, after or both before and after radiation treatment. The chemotherapeutic agents used are known in the art and their dosages will vary depending on the size of the original breast tumor, extent of metastasis, and the pathologic and biological/biochemical features of the tumor as known in the art. Chemotherapeutic agents typically used include cyclophosphamide, methotrexate, fluorouracil, doxorubicin hydrochloride, paclitaxel and combinations thereof and may be in a form that allows them to be administered orally, intravenously or by other methods known in the art. The dosages will vary as known in the art.

In a further embodiment of the present invention, a kit for treatment of a tumor, preferably a breast tumor and further preferably a breast tumor that has spread to a lymph node, preferably a parasternal lymph node, is provided. The kit includes standard medical devices as known in the art and are advantageously used in combination to treat a parasternal lymph node by irradiation through an internal thoracic vessel, preferably an artery. The kit includes an introducer, an internal mammary artery guiding catheter and a treatment catheter, all as described above. The kit may further contain a wire guide 200 configured to guide the internal mammary artery guiding catheter and a wire guide 220 configured to guide the treatment catheter as described above. Wire guide 200 preferably has a diameter of about 0.89 mm (0.035 in) whereas wire guide 220 preferably has a diameter of about 0.36 mm (0.014 in). A radioactive material is preferably disposed within the lumen of the treatment catheter.

The invention has been described above in detail, with specific reference to its preferred embodiments. It will be understood, however, that a variety of modifications and additions can be made to the apparatus and methods disclosed without departing from the spirit and scope of the invention. Such modifications and additions are desired to be protected. In addition, all references cited herein are indicative of the level of skill in the art and are hereby incorporated by reference in their entirety.

What is claimed is:

1. A method of treating a tumor, comprising;
   placing a radioactive material at a first predetermined site within an intact internal thoracic vessel for a time period sufficient to provide a therapeutically effective amount of radiation to treat said tumor.

2. The method of claim 1, wherein said placing comprises:
   positioning a first catheter having a lumen extending longitudinally therethrough in the lumen of said intact internal thoracic vessel; and
   positioning said radioactive material within said lumen of said first catheter.

3. The method of claim 2, wherein said positioning a first catheter comprises:
   advancing a second catheter having a lumen extending longitudinally therethrough into said intact internal thoracic vessel; and
   advancing said first catheter through said lumen of said second catheter.

4. The method of claim 1, wherein said internal thoracic vessel is an internal thoracic artery.

5. The method of claim 1, wherein said tumor is a breast tumor.

6. The method of claim 5, wherein said breast tumor has spread to a lymph node.

7. The method of claim 6, wherein said lymph node is a parasternal lymph node.

8. The method of claim 1, wherein said radioactive material is placed at successive predetermined sites for time periods sufficient to provide a therapeutically effective amount of radiation at each successive site after placing said radioactive material at said first predetermined site.

9. A method of treating a tumor, comprising:
   positioning a first catheter having a lumen extending longitudinally therethrough in the lumen of an intact internal thoracic vessel; and
   placing a radioactive material at a first predetermined site within said lumen of said first catheter for a time period sufficient to provide a therapeutically effective amount of radiation to treat said tumor.

10. The method of claim 9, wherein said positioning comprises:
    advancing a second catheter having a lumen extending longitudinally therethrough into said intact internal thoracic vessel; and
    advancing said first catheter through said lumen of said second catheter.

11. The method of claim 9, wherein said first catheter is a treatment catheter.

12. The method of claim 10, wherein said second catheter is an internal mammary artery guiding catheter.

13. The method of claim 9, said method further comprising treating said tumor with a chemotherapeutic agent after said time period sufficient to provide a therapeutically effective amount of said radiation.

14. The method of claim 9, said method further comprising treating said tumor with a chemotherapeutic agent prior to said positioning a first catheter having a lumen extending longitudinally therethrough in the lumen of an intact internal thoracic vessel.

15. The method of claim 9, wherein said tumor is a breast tumor.

16. The method of claim 15, wherein said breast tumor has spread to a lymph node.

17. The method of claim 16, wherein said lymph node is a parasternal lymph node.

18. The method of claim 9, wherein said radioactive material is inserted in said lumen of said first catheter by a remote afterloading machine.

19. The method of claim 9, wherein said internal thoracic vessel is an internal thoracic artery.

20. The method of claim 9, wherein said radioactive material is placed at successive predetermined sites for time periods sufficient to provide a therapeutically effective amount of radiation at each successive site after placing said radioactive material at said first predetermined site.

21. A method of treating a tumor, comprising:

positioning a first catheter having a proximal end, a distal end and a lumen extending longitudinally therethrough in a vessel that is continuous with a vessel that branches into an internal thoracic vessel;

advancing said first catheter into said internal thoracic vessel; and placing a radioactive material at a first predetermined site within said lumen of said first catheter for a time period sufficient to provide a therapeutically effective amount of radiation to treat said tumor.

22. The method of claim 21, wherein said positioning comprises:

placing a second catheter having a proximal end, a distal end and a lumen extending longitudinally therethrough into a brachial vessel;

advancing said second catheter into said internal thoracic vessel; and advancing said distal end of said first catheter through said lumen of said second catheter.

23. The method of claim 21, wherein said advancing said first catheter into said internal thoracic vessel comprises advancing said first catheter into an axillary vessel and a subclavian vessel.

24. The method of claim 21, wherein said tumor is a breast tumor.

25. The method of claim 24, wherein said breast tumor has spread to a lymph node.

26. The method of claim 25, wherein said lymph node is a parasternal lymph node.

27. The method of claim 21, wherein said vessel that is continuous with a vessel that branches into an internal thoracic vessel is a subclavian vessel.

28. The method of claim 21, wherein said vessel that is continuous with a vessel that branches into an internal thoracic vessel is a radial vessel.

29. The method of claim 21, wherein said radioactive material is inserted inside said lumen of said first catheter by a remote afterloading machine.

30. The method of claim 21, wherein said tumor is exposed to a chemotherapeutic agent prior to said positioning a first catheter.

31. The method of claim 21, wherein said tumor is exposed to a chemotherapeutic agent after providing said therapeutic amount of said radiation.

32. The method of claim 21, wherein said tumor is exposed to a chemotherapeutic agent prior to and after providing said therapeutically effective amount of said radiation.

33. The method of claim 21, wherein said internal thoracic vessel is an internal thoracic artery.

34. The method of claim 21, wherein said radioactive material is placed at successive predetermined sites for time periods sufficient to provide a therapeutically effective amount of radiation at each successive site after placing said radioactive material at said first predetermined site.

35. A method of treating a tumor, comprising:

placing a first catheter having a lumen extending longitudinally therethrough into a femoral vessel;

advancing said first catheter into an internal thoracic vessel;

advancing a second catheter through said lumen of said first catheter, said second catheter having a lumen extending longitudinally therethrough; and placing a radioactive material at a predetermined site within said lumen of said second catheter for a time period sufficient to provide a therapeutically effective amount of radiation to treat said tumor.

36. A method of treating a tumor, comprising:

placing a first catheter having a lumen extending longitudinally therethrough into a femoral artery;

advancing said first catheter into an internal thoracic artery;

advancing a second catheter through said lumen of said first catheter, said second catheter having a lumen extending longitudinally therethrough; and placing a radioactive material at a predetermined site within said lumen of said second catheter for a time period sufficient to provide a therapeutically effective amount of radiation to treat said tumor.

37. The method of claim 36, wherein said advancing said first catheter into an internal thoracic artery further comprises advancing said first catheter through an external iliac artery, a common iliac artery, an abdominal aorta, a thoracic aorta and a subclavian artery.

38. A treatment catheter, comprising:

a first elongated tube having a proximal end, a distal end and a lumen extending longitudinally therethrough;

a distal tip section comprising a proximal end and a distal end, said distal end of said distal tip section being closed, said proximal end of said distal tip section abutting said distal end of said first elongated tube;

a wire guide channel having a proximal end, a distal end and a lumen extending longitudinally therethrough, said wire guide channel extending along the longitude of said distal tip section; and a radioactive material disposed within said lumen of said first elongated tube for treating a tumor.

39. A treatment catheter, comprising:

a first elongated tube having a proximal end, a distal end and a lumen extending longitudinally therethrough;

a distal tip section comprising a proximal end, a distal end and a lumen extending longitudinally therethrough, said distal end of said distal tip section being closed, said proximal end of said distal tip section abutting said distal end of said first elongated tube;

a wire guide channel having a proximal end, a distal end and a lumen extending longitudinally therethrough, said wire guide channel extending along the longitude of said distal tip section; and a radioactive material disposed within said lumen of said first elongated tube for treating a tumor.

40. A kit for treatment of a tumor, said kit comprising:

an introducer;

a first catheter having a proximal end, a distal end and a lumen extending longitudinally therethrough, said distal end having a curved configuration, said catheter configured to introduce a second catheter inside a vascular passageway; and a second catheter comprising:

a first elongated tube having a proximal end, a distal end and a lumen extending longitudinally therethrough;

a distal tip section having a proximal end and a distal end, said distal end of said distal tip section being closed, said proximal end of said distal tip section abutting said distal end of said first elongated tube;

a wire guide channel having a proximal end, a distal end and a lumen extending longitudinally therethrough, said wire guide channel extending along the longitude of said distal tip section; and a radioactive material disposed within said lumen of said first elongated tube for treating said tumor.

41. The kit of claim 40, said kit further comprising a wire guide configured to guide said first catheter.

42. The kit of claim 40, said kit further comprising a wire guide configured to guide said second catheter.

43. The kit of claim 40, wherein said first catheter is an internal mammary artery guiding catheter.

44. The kit of claim 40, wherein said second catheter is a treatment catheter.

45. A kit for treatment of a tumor, said kit comprising;

an introducer;

a first catheter having a proximal end, a distal end and a lumen extending longitudinally therethrough, said distal end having a curved configuration, said catheter configured to introduce a second catheter inside a vascular passageway; and a second catheter comprising:

a first elongated tube having a proximal end, a distal end and a lumen extending longitudinally therethrough;

a distal tip section having a proximal end, a distal end and a lumen extending longitudinally therethrough, said distal end of said distal tip section being closed, said proximal end of said distal tip section abutting said distal end of said first elongated tube;

a wire guide channel having a proximal end, a distal end and a lumen extending longitudinally therethrough, said wire guide channel extending along the longitude of said distal tip section; and a radioactive material disposed within said lumen of said first elongated tube for treating said tumor.

46. The kit of claim 45, said kit further comprising a wire guide configured to guide said first catheter.

47. The kit of claim 45, said kit further comprising a wire guide configured to guide said second catheter.

48. The kit of claim 45, wherein said first catheter is an internal mammary artery guiding catheter.

49. The kit of claim 45, wherein said second catheter is a treatment catheter.

* * * * *